United States Patent [19]
Tanaka et al.

[11] Patent Number: 6,063,938
[45] Date of Patent: May 16, 2000

[54] PROCESS FOR PRODUCING ε-CAPROLACTONE

[75] Inventors: Kazuo Tanaka; Kengi Nakaya; Atsushi Ohkoshi; Hideaki Fujita, all of Kurashiki, Japan

[73] Assignee: Mitsubishi Gas Chemical Company, Inc., Tokyo, Japan

[21] Appl. No.: 08/900,875

[22] Filed: Jul. 25, 1997

[30] Foreign Application Priority Data

Jul. 29, 1996 [JP] Japan .................................. 8-199143

[51] Int. Cl.⁷ .................................................. C07D 309/00
[52] U.S. Cl. ............................................................ 549/273
[58] Field of Search ............................................ 549/273

[56] References Cited

U.S. PATENT DOCUMENTS 5,068,361  11/1991  Richter et al. ........................... 549/273

FOREIGN PATENT DOCUMENTS

| 0020952 | 5/1980 | European Pat. Off. . |
| 0026311 | 8/1980 | European Pat. Off. . |
| 0059655 | 2/1982 | European Pat. Off. . |
| 53-34789 | 3/1978 | Japan . |
| 57-42684 | 3/1982 | Japan . |
| 5-1054 | 1/1993 | Japan . |
| 9-87273 | 3/1997 | Japan . |

*Primary Examiner*—John Kight
*Assistant Examiner*—Raymond Covington
*Attorney, Agent, or Firm*—Armstrong, Westerman, Hattori, McLeland & Naughton

[57] ABSTRACT

Disclosed is a process for producing ε-caprolactone which comprises distilling a reaction mixture obtained by oxidation of cyclohexanone to separate impurities, wherein ε-caprolactone separated in a rectifying column is contacted with an oxygen-containing gas and then distilled. Thereby, a high quality of ε-caprolactone of in which no coloration occurs during long time preservation can be produced by industrial advantages.

5 Claims, 1 Drawing Sheet

PROCESS FOR PRODUCING ε-CAPROLACTONE

BACKGROUND OF THE INVENTION

1) Field of the Invention

The present invention relates to a process for producing ε-caprolactone. ε-caprolactone is useful as a raw material of ε-caprolactam which is used as a raw material of nylon resin, or a raw material of polyurethane.

2) Prior Art

ε-caprolactone is a high boiling point liquid with excellent reactivity and used as a raw material of polyesterpolyol, urethane resin, etc.

Thus, polyesterpolyol for polyurethane and high molecular weight polyesterpolyol which are produced from ε-caprolactone, are used as blend material for improvement of properties of various resins.

When polyesterpolyol obtained from ε-caprolactone is blended with polyethylene, gloss transparency and blocking preventive ability are improved. When it is blended with polyvinyl chloride, low temperature embrittlement of polyvinyl chloride is improved. However, properties of ε-caprolactone as raw material, particularly, appearance (coloration, etc.) of ε-caprolactone often have an influence also upon appearance, weather resistance, etc., of blended various resins.

As treatments for such ε-caprolactone, particularly, heretofore, improvement of purity by repeat of distillation, preservation under nitrogen atmosphere and addition of a stabilizer such as p-methoxyphenyol, tridecylphosphite, 2,6-ditertiary-butyl-4-methylphenol, etc., have been conducted. Japanese Patent Kokai (Laid-open) No. 5-1054 describes to use a hydrotalcite compound as the adsorbent.

ε-caprolactone is produced by oxidation of cylohexanone. As processes for producing ε-caprolactone by oxidation of cyclohexanone, there are a co-oxidation process wherein both cyclohexanone and aldehyde are oxidized and a peracid oxidation process using organic peracid as an oxidizing agent.

When conventional distillation processes are applied for separation of the intended substance from a reaction mixture obtained by such oxidation of cyclohexanone, polymerization loss of ε-caprolactone becomes large and the yield is lowered.

The loss of ε-caprolactone in the distillation step is due to high boiling substances contained in the reaction product. Japanese Patent Kokai (Laid open) No. 53-34789 describes a process wherein, in order to prevent the loss, the high boiling substances are removed with a thin film type evaporator provided prior to the distillation step of unreacted cyclohexanone. However, in the above-mentioned process an expensive evaporator is necessary in addition to heat evaporator attached to a distillation column and both cost of apparatus and energy is increased.

Japanese Patent Kokai (laid-open) No. 57-42684 describes to distill off low boiling substances from a reaction mixture obtained by organic peracid oxidation of cyclohexanone and then to distill in an apparatus provided with a single pass type thin film evaporator. However, in the above-mentioned process, a peracid oxidation process using expensive organic peracid is applied. When the co-oxidation process is applied to the above-mentioned process instead of the peracid oxidation process, loss of ε-caprolactone is large since polymerization remarkably occurs. Further in the above-mentioned process a severe burden in the aspect of economy is imposed since it is necessary to apply the expensive single pass type thin film evaporator as a reboiler.

As treatment of ε-caprolactone, as described above, when distillation is repeated, its appearance becomes colorless and transparent just after the distillation, but coloration often occurs during long time preservation. Also in preservation under nitrogen atmosphere, sufficient improvement for coloration cannot be expected. Addition of a stabilizer causes deterioration of appearance of urethane resin which is produced using lactonepolyol. Use of an adsorbent causes a problem that it is considerably expensive.

Although various improvements of process for loss of ε-caprolactone in the distillation step have been tried, a severe burden in the aspect of economy is imposed since expensive single pass type thin film evaporator is applied. Therefore, further improvement is required.

SUMMARY OF THE INVENTION

An object of the present invention, under the above-mentioned situation, is to provide a process for producing a high quality of ε-caprolactone with industrial advantages in which no coloration occurs during long time preservation, without using expensive stabilizer or adsorbent.

As a result of study of process for producing ε-caprolactone by co-oxidation of both cyclohexanone and aromatic aldehyde, the inventors found that loss of ε-caprolactone is reduced by applying both a circular type reboiler and a single pass type thin film evaporator in a rectifying column (Japanese Patent Kokai (Laid-open No. 9-87273). According to the process, ε-caprolactone can be efficiently produced, but a thin film evaporator is necessary and also further improvement of quality of ε-caprolactone has been required.

As a result of further extensive study of process for producing ε-caprolactone for solving the above-mentioned problems, the inventors, the inventors found that (1) no coloration occurs during long time preservation by refining an oxidation reaction mixture by distillation and then contacting ε-caprolactone separated in a rectifying column with an oxygen-containing gas and removing color components as high boiling components by distillation and (2) ε-caprolactone can be obtained in a high yield by removing a portion of high boiling substances prior to removal of low boiling substances in a distillation column and withdrawing high boiling substances in a low concentrated state in the rectifying column and then treating it in said distillation column and (3) a high quality of ε-caprolactone in which no coloration occurs, can be obtained by maintaining a reactivity of aromatic aldehyde to 80 mol % or below in a process for producing ε-caprolactone by co-oxidation of both aromatic aldehyde and cyclohexanone, and accomplished the present invention.

That is, the first present invention provides a process for producing ε-caprolactone which comprises distilling a reaction mixture obtained by oxidation of cyclohexanone to separate impurities, wherein ε-caprolactone separated in a rectifying column is contacted with an oxygen-containing gas and then distilled.

The second present invention provides a process for producing ε-caprolactone according to the process of the first invention, which comprises a first distillation step for removing high boiling substances from a reaction mixture obtained by oxidation of cyclohexanone by distillation, a second distillation step for removing low boiling substances and a third distillation step for removing high boiling substances in a rectifying column, and withdrawing high boiling components in a low concentrated state of 5 to 30% by weight in the third distillation step and then treating it in the first distillation step.

The third present invention provides a process for producing ε-caprolactone according to the process of the first invention, wherein the reaction mixture in the process of the first present invention is obtained by oxidizing a mixture of aromatic aldehyde and cyclohexanone with molecular oxygen in a liquid phase so as to maintain a reactivity of aromatic aldehyde to 80 mol % or below.

DETAILED DESCRIPTION OF THE INVENTION

Figure 1:
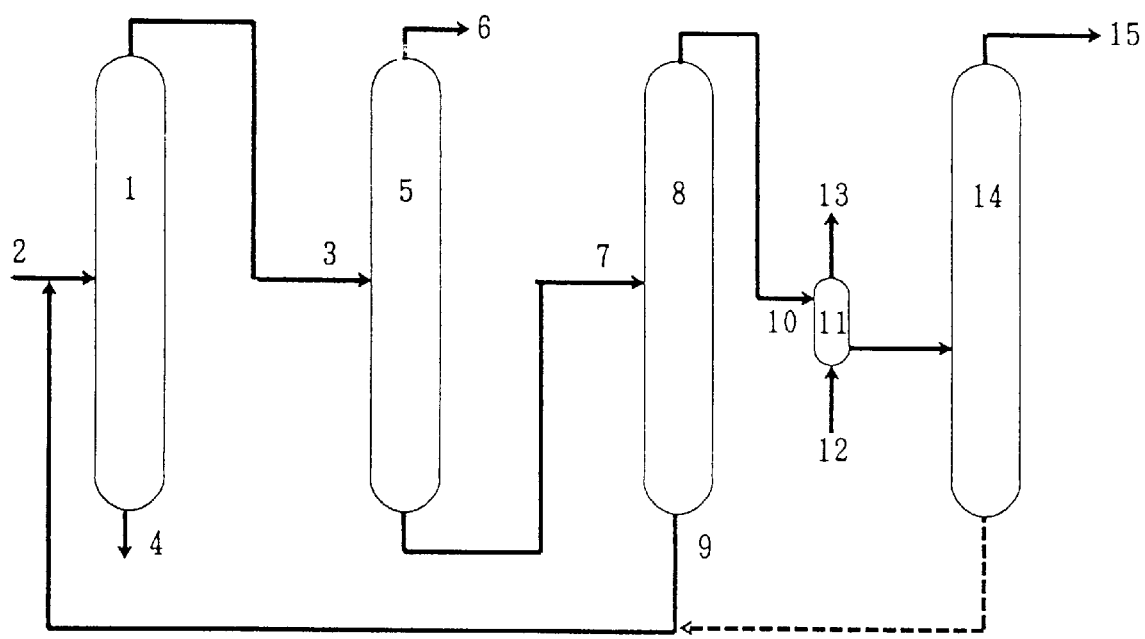
FIG. 1 shows one example of flow diagram in the process for producing ε-caprolactone in the present invention.

The present invention will be described in detail below.

As described above, as processes for producing ε-caprolactone by oxidation of cyclohexanone, there are a co-oxidation process wherein both cyclohexanone and aldehyde are oxidized and a peracid oxidation process using organic peracid as an oxidizing agent. The process of the present invention is not limited to both the above-mentioned processes.

Examples of organic peracid using in the peracid oxidation process include peracetic acid, peroxypropionic acid, peroxyisobutyric acid, etc. The organic peracid is used usually in the form of a solution of acetone, ethyl acetate, acetic acid, etc. The organic peracids oxidize cyclohhexanone to change it to ε-caprolactone and organic peracids themselves change to organic acids such as acetic acid, propionic acid, isobutyric acid, etc., having a lower boiling point than that of ε-caprolactone.

Examples of aldehyde using in the co-oxidation process include aliphatic aldehydes and aromatic aldehydes. Both aldehyde and cyclohexanone are co-oxidized, generally, with air, whereby both organic acid corresponding to the aldehyde and ε-caprolactone are produced.

As aliphatic aldehydes in the co-oxidation process, acetaldehyde is generally used. Examples of aromatic aldehyde include benzaldehyde, tolualdehyde, dimethylbenzaldehyde, trimethylbenzaldehyde, ethylbenzaldehyde, cuminaldehyde, butylbenzaldehyde, methoxybenzaldehyde, phenoxybenzaldehyde, cyclohexylbenzaldehyde, bisphenylbenzaldehyde, etc.

Impurities are removed from a reaction mixture containing ε-caprolactone obtained by the reaction with cyclohexanone according to the peracid oxidation process or co-oxidation process, thereby obtaining refined ε-caprolactone.

The reaction mixture in the peracid oxidation process contains ε-caprolactone and impurities including unreacted cyclohexanone, unreacted organic peracid, solvents of organic peracid, e.g., ethyl acetate, organic acids such as acetic acid, etc., caprolactone oligomers, caprolactone polymers, oxycaproic acid, adipic acid, other by-products with indefinite structure, etc.

The reaction mixture in the co-oxidation process with aldehyde contains ε-caprolactone and impurities including unreacted cyclohexanone, acetic acid, acetaldehyde, adipic acid, caprolactone oligomers, caprolactone polymers, oxycaproic acid, etc.

The reaction mixture obtained by the co-oxidation process using 2, 4-dimethylbenzaldehyde as aromatic aldehyde contains ε-caprolactone and impurities including 2, 4-dimethyl benzoic acid, cyclohexanone, 2, 4-dimethylbenzaldehyde, caprolactone oligomers, other by-products with indefinite structure, etc.

The process of the first present invention comprises distilling a reaction mixture obtained by oxidation of cyclohexanone to refine and then contacting ε-caprolactone separated in a rectifying column with an oxygen-containing gas and then distilling to separate color components as high boiling components.

That is, in the peracid oxidation process using peracid, high boiling substances such as adipic acid, caprolactone oligomers, caprolactone polymers, oxycaproic acid, etc. as by-products are initially removed and then unreacted cyclohexanone, ethyl acetate, acetic acid, etc. as solvent are removed as low boiling substances by distillation.

Further, in the co-oxidation process with aldehyde, high boiling substances such as adipic acid, caprolactone oligomers, caprolactone polymers, oxycaproic acid, etc. as by-products are initially removed and then unreacted cyclohexanone, acetic acid, acetaldehyde, etc., are removed as low boiling substances by distillation.

In the co-oxidation process with 2,4-dimethylbenzaldehyde, unreacted cyclohexanone (boiling point 155.6° C.) is initially removed and then 2, 4-dimethyl benzoic acid (boiling point 267° C.) and 2, 4-dimethylbenzaldehyde (boiling point 225° C.) as high boiling substances are removed.

The reaction mixture obtained by oxidation of cyclohexanone according to the above-mentioned processes is distilled to refine and then remained high boiling substances are removed in a rectifying column and thus obtained ε-caprolactone is contacted with an oxygen-containing gas and then color components are removed as high boiling components by distillation, thereby obtaining ε-caprolactone (boiling point 235.3° C.) as product.

The distillation redefining is conducted according to a conventional process and usually according to vacuum distillation since it is necessary to be conducted at as a low temperature as possible in order to avoid quality change during the distillation.

The temperature to contact ε-caprolactone separated in a rectifying column with an oxygen-containing gas is in the range of a room temperature to 200° C. and preferably in the range of 100 to 150° C. When the temperature is too low, contact time is prolonged. Further, when the temperature is too high, it is not preferable because polymerization of ε-caprolactone readily occurs.

The pressure to contact ε-caprolactone separated in a rectifying column with an oxygen-containing gas is usually atmospheric pressure to 10 kg/cm² (absolute).

The oxygen-containing gas is continuously fed. ε-caprolactone entrained in waste gas at a cooler is condensed and then recovered.

The partial pressure of oxygen to contact with ε-caprolactone is 0.0002 to 1.0 kg/cm² (absolute) and preferably 0.0005 to 0.5 kg/cm² (absolute). The partial pressure of oxygen in a contact vessel is calculated from oxygen concentration in the waste gas from the above-mentioned cooler. When the partial pressure of oxygen is too high, quality change of ε-caprolactone readily occurs, depending upon contact temperature and hold-up time. When the partial pressure of oxygen is too low, it is not preferably because coloration occurs during long time preservation.

The molar ratio of oxygen to ε-caprolactone is in the range of 0.0002 to 0.1 whereas over the above-mentioned range of molar ratio of oxygen, further improvement for coloration cannot be provided.

The treating time is in the range of 5 minutes to 10 hours, depending upon temperature, partial pressure of oxygen, etc.

According to the above-mentioned process, substances to cause coloration contained in a small quantity in ε-caprolactone become high boiling substances by contacting ε-caprolactone with an oxygen-containing gas. Therefore, they are removed by distillation. The substances to cause coloration which have been changed to high boiling substances by contacting with oxygen can be separated by simple distillation since there is considerable difference of boiling point between them and ε-caprolactone and may be rectified by applying reflux, if necessary. When the purity of ε-caprolactone is high, the treatment of contact with an oxygen-containing gas provides improvement effect for coloration. When ε-caprolactone contains a large amount of impurities, on the contrary, a large amount of color substances are generated. Therefore, it is necessary to contact ε-caprolactone separated in a rectifying column with an oxygen-containing gas.

Thus, ε-caprolactone separated in a rectifying column is contacted with an oxygen-containing gas and then distilled, whereby substances to cause coloration are removed and a product in which quality change with the passage of time is small, is obtained.

The process of the second present invention (hereinafter, referred to as "the second process") comprises, in order to increase a refining yield of ε-caprolactone, removing in advance a portion of high boiling substances prior to removal of low boiling substances in the oxidation reaction mixture. That is, the second process comprises removing a portion of high boiling substances from the reaction mixture obtained by oxidation of cyclohexanone in a first distillation step and then removing low boiling substances such as cyclohexanone, etc., in a second distillation step and finally separating ε-caprolactone from remained high boiling substances in a rectifying column in a third distillation step.

The term "high boiling substances" in the first distillation step means substances having higher boiling point than that of ε-caprolactone. When ε-caprolactone is obtained from organic peracid such as peracetic acid and cyclohexanone, produced high boiling substances contain caprolactone oligomers, caprolactone polymers, oxycaproic acid, adipic acid, other by-products with indefinite structure, etc. Further, In case of peracid oxidation process using organic peracid from aromatic aldehyde or co-oxidation process of aromatic aldehyde and cyclohexanone, the quantity of obtained aromatic carboxylic acid is larger than that of ε-caprolactone. In this case, the aromatic carboxylic acid, caprolactone oligomers, caprolactone polymers, oxycaproic acid, adipic acid, other by-products with indefinite structure become high boiling substances.

A portion of the high boiling substances is removed in the first distillation step and then substances such as cyclohexanone having lower boiling point than that of ε-caprolactone are removed in the second distillation step and finally ε-caprolactone is separated from remained high boiling substances in a rectifying column in the third distillation step.

In the distillation refining in the rectifying column, in order to increase the refining yield of ε-caprolactone, it is necessary to remove a small amount of high boiling components in the feed liquid and make high the concentration of high boiling components at bottom section of the rectifying column. However, when concentration, i.e., enrichment is promoted, polymerization loss of ε-caprolactone is increased. Further, in order to reduce concentration, i.e., enrichment of high boiling components, when the amount withdrawn from the bottom section is continuously increased, ε-caprolactone entraining in the high boiling components is increased, so that the refining yield is lowered.

In order to reduce polymerization loss in each of the distillation columns including the rectifying column, it is preferable to keep the temperature as low as possible and shorten hold-up time at the bottom section.

In the second process, in order to increase the refining yield of ε-caprolactone, high boiling substances obtained from the rectifying column in the third distillation step are treated in the first distillation step. That is, it is necessary to make high the concentration of high boiling components at the bottom section of the rectifying column. However, when concentration, i.e., enrichment is promoted, it is necessary to increase a withdrawing amount from the bottom section of the rectifying column since polymerization loss of ε-caprolactone is increased. The high boiling substances from the rectifying column in the third distillation step are treated in the first distillation step, whereby ε-caprolactone is recovered in the first distillation step and lowering of refining yield of ε-caprolactone due to increase of withdrawing amount from the bottom section of the rectifying column is avoided.

It is necessary to maintain the concentration of high boiling components in the bottom liquid of rectifying column to 5 to 50% by weight, preferably 10 to 20% by weight because above 30% by weight the polymerization loss is acceleratedly increased. The polymerization loss is reduced to minimum by maintaining high boiling components to such concentration.

One example of flow diagram in the process for producing ε-caprolactone in the present invention is shown in FIG. 1. The case of distilling a reaction mixture obtained by co-oxidation of cyclohexanone and 2,4-dimethylbenzaldehyde is explained below in detail.

In FIG. 1, the reaction mixture obtained by oxidation of cyclohexanone, as the first distillation step, is introduced into high boiling substance separation column 1 via flow path 2 and high boiling substances are removed via flow path 4. The distillate separated high boiling substances from high boiling substance separation column 1, as the second distillation step, is introduced into low boiling substance separation column 5 via flow path 3 and low boiling substances are removed via flow path 5.

Then, the bottom liquid of low boiling substance separation column 5, as the third distillation step, is introduced into rectifying column 8 via flow path 7 and high boiling substances are withdrawn in a low concentrated state of 5 to 30% by weight via flow path 9 and introduced into high boiling substance separation column 1 of the first distillation step via flow path 9. ε-caprolactone from rectifying column 8 is introduced into contact vessel 11 via path flow 10 and contacted with an oxygen-containing gas (air) from flow path 12 in contact vessel 11 and the off gas is exhausted via flow path 13. ε-caprolactone after contacting with the oxygen-containing gas is introduced into product distillation column 14 and substances to cause coloration as high boiling substances are removed, thus obtaining ε-caprolactone as product via path flow 15. Also a slight amount of high boiling substances separated in product distillation column 14 can be treated in high boiling substance separation column 1 of the first distillation step.

In the process of the third present invention (hereinafter, referred to as "the third process"), the reaction mixture in the process of the first present invention is obtained by oxidizing a mixture of aromatic aldehyde and cyclohexanone with molecular oxygen in a liquid phase so as to maintain a reactivity of aromatic aldehyde to 80 mol % or below.

In the third process, aromatic aldehyde using as a raw material is the same as described above. The preferable feed ratio (molar ratio) to a reactor of cyclohexanone to aromatic aldehyde is in the range of 0.7/1 to 20/1. When the feed ratio is below the above-mentioned range, by-production of aryl formate is increased, whereas over the above-mentioned range, the yield of ε-caprolactone is lowered.

In the third process, by the co-oxidation reaction of aromatic aldehyde, the corresponding aromatic carboxylic acid is obtained.

The co-oxidation reaction can be conducted by batchwise, semi-continuous process of continuous process, among which continuous process is preferable.

The co-oxidation process is conducted usually in the absence of a solvent. However, if necessary, a solvent may be used. Examples of the solvent include hydrocarbons such as hexane, cyclohexane, benzene, toluene, xylene, etc., ketones such as acetone, methylethylketone, diisobutylketone, etc., esters such as ethyl acetate, butyl acetate, methyl benzoate, etc., nitriles such as acetonitrile, benzonitrile, etc., low organic carboxylic acids such as formic acid, acetic acid, propionic acid, etc.

Molecular oxygen is used as an oxidant of the co-oxidation reaction. The molecular oxygen is fed in the form of pure oxygen, air, oxygen-enriched air or a mixed gas of oxygen and inert gas (carbon dioxide, nitrogen, etc), among which air is usually used.

The reaction temperature is in the range of −20 to 150° C. and preferably in the range of 20 to 60° C. When the reaction temperature is made higher, the reaction rate is increased, but selectivity to aromatic carboxylic acid and ε-caprolactone is lowered and both color and quality of ε-caprolactone are deteriorated. Further, when the reaction temperature is made lower. the reaction rate is decreased. ε-caprolactone with good color and excellent quality can be obtained by selected the above-mentioned preferable temperature range.

The reaction pressure is usually atmospheric pressure to 60 kg/cm$^2$ G and preferably 10 to 40 kg/cm$^2$ G. When the reaction pressure is made higher, the reaction rate is increased and the yield becomes high. It is preferable to conduct the reaction under an applied pressure since it is possible to prevent a solvent evaporating toward the outside of the reaction system. However, when the reaction pressure is above 60 kg/cm$^2$ G, the reaction is usually conducted within the above-mentioned range since no effect of the applied pressure is provided.

The co-oxidation can be conducted even in the absence of a catalyst. It is preferable to use a metal catalyst including cobalt, manganese, iron, platinum, palladium, vanadium, ruthenium, zirconium, aluminum, beryllium, copper, etc., among which, particularly, cobalt catalyst is preferable.

The amount of cobalt catalyst to the whole weight of reaction liquid is 0.01 to 50 ppm and preferably 0.1 to 10 ppm. When the amount of cobalt catalyst is below 0.01 ppm, the reaction rate is low, whereas above 50 ppm the yield of ε-caprolactone is lowered.

The hold-up time of reactor in the co-oxidation is 5 minutes to 10 hours and preferably 10 to 120 minutes. When the hold-up time is too short, the reactivity becomes low, so that productivity is lowered. Further, when hold-up time is too long, side reaction readily occurs and both production of color components and a trace amount of inseparable impurities are increased, so that it becomes difficult to obtain ε-caprolactone with good color.

In the co-oxidation reaction, ε-caprolactone with good color can be obtained by maintaining an oxidation reactivity of aromatic aldehyde to 80 mol % or below and preferably to 70 mol % or below. In order to ensure such oxidation reactivity of aromatic aldehyde, it is effective to keep the above-mentioned preferable range of both the reaction temperature and the hold-up time. When the oxidation reactivity of aromatic aldehyde is above 80 mol %, color components to substances to cause color components are produced to the degree which cannot be neglected, so that it becomes difficult to obtain ε-caprolactone with good color.

As described above, according to the process of the first present invention, ε-caprolactone can be preserved for a long time without occurrence of coloration by contacting ε-caprolactone from the rectifying column with an oxygen-containing gas and removing color components as high boiling components by distillation.

The process is industrially excellent since it can be easily conducted without using expensive stabilizer and adsorbent.

According to the process of the second present invention, the loss of ε-caprolactone is remarkably reduced and the refining yield is improved by withdrawing a bottom liquid of the rectifying column in the third distillation in a low concentrated state and then treating in the high boiling substance separation column of the first distillation step. According the process, it is economically advantageous since no thin film evaporator is required.

According to the process of the third present invention, a high quality of ε-caprolactone with good color and less change with the lapse of time can be obtained by maintaining the reactivity of aromatic aldehyde to 80 mol % or below in a process for producing ε-caprolactone by co-oxidation of both aromatic aldehyde and cyclohexanone.

According the above-mentioned processes, a high quality of ε-caprolactone in which no coloration occurs during long time preservation, can be produced with industrial advantages and the industrial significance of the present invention is large.

PREFERRED EMBODIMENTS OF THE INVENTION

Some of the preferred embodiments of the present invention will be described in detail below, referring to Examples and Reference Examples, which are not intended to limit the scope of the present invention.

In the measurement of APHA in Examples, according to the method described in JIS K 1557. 6.2, a sample was put in a color tube and then its color was compared with that of APHA standard liquid.

REFERENCE EXAMPLE 1

Co-oxidation of Both Cyclohexanone and 2,4-dimethylbenzaldehyde

A mixture liquid containing 80% by weight (hereinafter "wt %") of cyclohexanone, 20 wt % of 2,4-dimethylbenzaldehyde and 1 ppm (as cobalt) as cobalt naphthenate as catalyst was fed to a flow pass type autoclave having interior capacity of 12 L, provided with a stirrer at the rate of 3000 g/hr. The continuous reaction was conducted at a reaction temperature of 35° C. under a pressure of 25 kg/cm$^2$G while adjusting air concentration in the off gas to 10 vol %. The reaction mixture thus obtained was analyzed. The components of the reaction mixture were ε-caprolactone 12.3 wt %, 2,4-dimethylbenzoic acid 18.1 wt %, 2,4-dimethylbenzaldehyde 2.7 wt %, cyclohexanone 66.1 wt % and other components 0.8 wt %.

REFERENCE EXAMPLE 2

First Distillation Step

The reaction mixture obtained in Reference Example 1 was continuously fed to a falling film evaporator at the rate of 8000 g/hr and 55 wt % of cyclohexanone to the feed liquid was separated by evaporation under 25 mmHg. The purity of cyclohexanone in the distillate was 95.6 wt %. The concentrated liquid was fed to a high boiling substance separation column (theoretical plate of 10 plates) and further distilled under 10 mmHg and 2,4-dimethylbenzoic acid and high boiling substances were withdrawn as a bottom liquid of the high boiling substance separation column. The distillate was obtained at the rate of 2097 g/hr from the top section of the high boiling substance separation column. The components of the distillate from the top section were ε-caprolactone 39.8 wt %, 2,4-dimethylbenzaldehyde 8.2 wt %, cyclohexanone 51.6 wt % and other components 0.4 wt %.

REFERENCE EXAMPLE 3

Second Distillation Step and Third Distillation Step

The total number (2097 g/hr) of the high boiling substance separation column top distillate in Reference Example 2 was fed to a low boiling substance separation column (theoretical plate of 30 plates) of the second distillation step, and cyclohexanone, 2,4-dimethylbenzaldehyde and other low boiling components were distilled out from the top section. Further, crude ε-caprolactone (purity 99.0 wt %) from the bottom section of the low boiling substance separation column was fed to a rectifying column (theoretical plate of 30 plates) of the third distillation step at the rate of 826 g/hr. At first, the bottom liquid was not withdrawn. So, the temperature of the bottom liquid in the rectifying column was elevated, the operation was stabilized by maintaining the withdrawing amount to 126 g/hr. The concentration of high boiling components in rectifying column bottom section in a steady state was measured. The concentration was 51.2 wt %. The distillate amount of ε-caprolactone from the top section of the rectifying column was 700 g/hr.

The refining yield (refined ε-caprolactone thus obtained to ε-caprolactone in feed liquid of the rectifying column) was 85.6 wt %. The loss of ε-caprolactone from the bottom section of the rectifying column was 7.4 wt % and the quality change loss of ε-caprolactone was 7.0 wt %.

The color of ε-caprolactone thus obtained from the top section of the rectifying column was APHA5. The ε-caprolactone thus obtained was preserved at a room temperature for one month under nitrogen atmosphere. As a result, its color was changed to APHA 35.

The operation conditions of the low boiling substance separation column and the rectifying column are shown in Table 1.

EXAMPLE 1

350 g of ε-caprolactone (APHA5) just after obtained from the top section of the rectifying column in Reference Example 3 was charged into a glass vessel of 500 cc and heated up to 150° C. under nitrogen atmosphere and then air was introduced thereto at the rate of 50 ml/min, and the state was maintained for 60 min under atmospheric pressure. Then, cooled ε-caprolactone was simple distilled under 25 Torr. 95 wt % of the charge amount was distilled out and its color was measured. Its color was APHA5. The distillate was preserved at a room temperature for one month under nitrogen atmosphere and then its color was measured. Its color was APHA5 and no color change was observed.

COMPARATIVE EXAMPLE 1

350 g of ε-caprolactone as a starting material used in Example 1 was rectified in a distillation column (theoretical plate of 30 plates) under 25 Torr in a reflux ratio of 2.3 without contacting with an oxygen-containing gas. 95 wt % of the charge amount was distilled out and its color was measured. Its color was APHA5. The distillate was preserved at a room temperature for one month under nitrogen atmosphere and then its color was measured. Its color was APHA 30.

COMPARATIVE EXAMPLE 2

The same operation as in Example 1 except that nitrogen gas was introduced instead of air, was conducted. The color of ε-caprolactone after simple distillation was APHA5. The distillate was preserved at a room temperature for one month under nitrogen atmosphere and its color was measured. Its color was APHA30.

EXAMPLE 2

350 g of ε-caprolactone as a starting material used in Example 1 was charged into a glass vessel of 500 cc and heated up to 100° C. under nitrogen atmosphere and then nitrogen gas containing 5 vol % of oxygen was introduced thereto at the rate of 30 ml/min, and the state was maintained for 3 hours under atmospheric pressure. Then, cooled ε-caprolactone was simple distilled. 95 wt % of the charge amount was distilled out and its color was measured. Its color was APHA5. The distillate was preserved at a room temperature for one month under nitrogen atmosphere and its color was measured. Its color was APHA5 and no color change was observed.

EXAMPLE 3

The bottom liquid from the rectifying column of the third distillation step in Reference Example 3 was withdrawn at the rate of 168 g/hr. and fed to the high boiling substance separation column of the first distillation step in Reference Example 2. The concentration of high boiling components in the liquid withdrawn from the bottom section of the rectifying column in a steady state was 10.2 wt %.

The distillation was under the same conditions as in Reference Example 2. The distillate from the top section of the high boiling substance separation column was obtained in the rate of 2243 g/hr. and the components of the distillate were ε-caprolactone 43.7 wt %, 2,4-dimethylbenzaldehyde 7.7 wt %, cyclohexanone 48.2 wt % and other components 0.4 wt %.

When Example 3 was compared with Reference Example 2, ε-caprolactone in the distillate from the top section of the high boiling substance separation column increased by 146 g/hr and 96.9 wt % of ε-caprolactone entrained in the bottom liquid of the rectifying column was recovered.

EXAMPLE 4

The distillate from the top section of the high boiling substance separation column obtained in Example 3 was fed to the low boiling point substance separation column in Reference Example 3. Cyclohexanone, 2,4-dimethylbenzaldehyde and other low boiling components were distilled out from the top section. Further, crude ε-caprolactone from the bottom section of the low boiling substance separation column was fed to the rectifying column of the third distillation step in the rate of 972 g/hr.

The distilled amount of ε-caprolactone from the top section of rectifying column was 804 g/hr and the refining yield was 98.3 wt %. It was presumed that the quality change loss of ε-caprolactone in the rectifying column was 1.1 wt % and the quality change loss of ε-caprolactone in the high boiling substance separation column was 0.6 wt %.

The color of ε-caprolactone from the top section of the rectifying column was APHA5. It was preserved at a room temperature for one month under nitrogen atmosphere and its color was measured. Its color was APHA35. In Reference Example 3 wherein no recycling was conducted, the color of ε-caprolactone was APHA5 just after distillation and APHA 35 after preservation at a room temperature for one month under nitrogen atmosphere. According to this fact, it is presumed that even if the bottom liquid from the rectifying column is recycled to the high boiling substance separation column, no color change will occur.

Further, ε-caprolactone from the top section of the rectifying column was contacted with air and simple distilled under the same conditions as in Example 1. The color of the distillate just after the simple distillation was APHA5. The distillate was preserved at a room temperature for one month under nitrogen atmosphere and then its color was measured. Its color was APHA5 and no color change was observed.

EXAMPLE 5

3000 g of a mixture liquid containing 80% by weight of cyclohexanone, 20 wt % of 2,4-dimethylbenzaldehyde and 1 ppm (as cobalt) of cobalt naphthenate as catalyst was charged to a flow pass type autoclave having interior capacity of 6 L, provided with a stirrer and air was introduced thereto and then the reaction started. The mixture liquid was fed at the rate of 3000 g/hr. The reaction was conducted at a reaction temperature of 35° C. under a pressure of 25 kg/cm$^2$G while adjusting air concentration in the off gas to 10 vol % and maintaining the liquid level to a steady state. The reaction mixture was withdrawn continuously.

The withdrawn amount of the reaction mixture in a steady state is 3086 g/hr. The components of the reaction mixture were ε-caprolactone 7.92 wt %, 2,4-dimethylbenzoic acid 12.75 wt %, 2,4-dimethylbenzaldehyde 7.58 wt %, cyclohexanone 70.6 wt % and other components 1.15 wt %. The hold-up time was 1.0 hr and the reactivity of 2,4-dimethylbenzaldehyde was 61.0 mol %.

Cyclohexanone was initially separated from the reaction mixture thus obtained in a thin film evaporator and then 2,4-dimethylbenzoic acid and other high boiling substances were removed by distillation, and remained cyclohexanone, unreacted 2,4-dimethylbenzaldehyde and other low boiling substances were removed by further distillation and finally ε-caprolactone was obtained by rectification. The color of ε-caprolactone thus obtained was APHA5 just after distillation.

A portion of ε-caprolactone thus obtained was contacted with air under the same conditions as in Example 1 and then simple distilled and its color was measured. Its color was APHA5 just after distillation. The distillate was preserved at a room temperature for one month under nitrogen atmosphere and then its color was measured. Its color was APHA5 and no color change was observed.

Further, a portion of ε-caprolactone which was not contacted with oxygen, was preserved at a room temperature for one month under nitrogen atmosphere and then its color was measured. Its color was APHA15.

COMPARATIVE EXAMPLE 3

The oxidation reaction was conducted in the same manner as in Example 5 except that the feed rate of the mixture liquid was 1200 g/hr. The withdrawing amount in a steady state was 1247 g/hr and hold-up time was 2.4 hr and the reactivity of 2,4-dimethylbenzaldehyde was 82 mol %. The reaction mixture was refined in the same manner as in Example 5. The color of ε-caprolactone thus obtained was APHA10 just after distillation.

A portion of ε-caprolactone thus obtained was was contacted with air under the same conditions as in Example 1 and simple distilled and its color was measured. Its color was APHA10 just after distillation. The distillate was preserved at a room temperature for one month under nitrogen atmosphere and then its color was measured. Its color was APHA10 and no color change was observed.

Further, a portion of ε-caprolactone which was not contacted with oxygen, was preserved at a room temperature for one month under nitrogen atmosphere and then its color was measured. Its color was APHA30.

EXAMPLE 6

The oxidation reaction was conducted in the same manner as in Example 5 except that the reaction temperature was 45° C. and cobalt and in the mixture liquid was 0.18 ppm. The withdrawing amount in a steady state was 3093 g/hr and hold-up time was 1.0 hr and the reactivity of 2,4-dimethylbenzaldehyde was 65 mol %. The reaction mixture was refined in the same manner as in Example 5. The color of ε-caprolactone thus obtained was APHA5 just after distillation.

A portion of ε-caprolactone thus obtained was was contacted with air under the same conditions as in Example 1 and simple distilled and its color was measured. Its color was APHA5 just after distillation. The distillate was preserved at a room temperature for one month under nitrogen atmosphere and then its color was measured. Its color was APHA5 and no color change was observed.

Further, a portion of ε-caprolactone which was not contacted with oxygen, was preserved at a room temperature for one month under nitrogen atmosphere and then its color was measured. Its color was APHA15.

EXAMPLE 7

The oxidation reaction was conducted in the same manner as in Example 5 except that the reaction temperature was 40° C. The withdrawn amount in a steady state was 3103 g/hr and hold-up time was 1.0 hr and the reactivity of 2,4-dimethylbenzaldehyde was 72 mol %. The reaction mixture was refined in the same manner as in Example 5. The color of ε-caprolactone thus obtained was APHA5 just after distillation.

A portion of ε-caprolactone thus obtained was contacted with air under the same conditions as in Example 1 and simple distilled and its color was measured. Its color was APHA5 just after distillation. The distillate was preserved at a room temperature for one month under nitrogen atmosphere and then its color was measured. Its color was APHA5 and no color change was observed.

Further, a portion of ε-caprolactone which was not contacted with oxygen, was preserved at a room temperature for one month under nitrogen atmosphere and then its color was measured. Its color was APHA15.

EXAMPLE 8

The oxidation reaction was conducted in the same manner as in Example 5 except that the reaction temperature was 40° C. and initial charge amount was 1500 g. The withdrawn amount in a steady state was 3057 g/hr and hold-up time was 0.5 hr and the reactivity of 2,4-dimethylbenzaldehyde was 40 mol %. The reaction mixture was refined in the same manner as in Example 5. The color of ε-caprolactone thus obtained was APHA5 just after distillation.

A portion of ε-caprolactone thus obtained was was contacted with air under the same conditions as in Example 1 and simple distilled and its color was measured. Its color was APHA5 just after distillation. The distillate was preserved at a room temperature for one month under nitrogen atmosphere and then its color was measured. Its color was APHA5 and no color change was observed.

Further, a portion of ε-caprolactone which was not contacted with oxygen, was preserved at a room temperature for one month under nitrogen atmosphere and then its color was measured. Its color was APHA10.

COMPARATIVE EXAMPLE 4

The oxidation reaction was conducted in the same manner as in Example 5 except that the reaction temperature 40° C. and the feed rate was 750 g/hr. The withdrawn amount in a steady state was 782 g/hr and hold-up time was 3.8 hr and the reactivity of 2,4-dimethylbenzaldehyde was 89 mol %. The reaction mixture was refined in the same manner as in Example 5. The color of ε-caprolactone thus obtained was APHA15 just after distillation.

A portion of ε-caprolactone thus obtained was contacted with air under the same conditions as in Example 1 and simple distilled and its color was measured. Its color was APHA15 just after distillation. The distillate was preserved at a room temperature for one month under nitrogen atmosphere and then its color was measured. Its color was APHA15 and no color change was observed.

Further, a portion of ε-caprolactone which was not contacted with oxygen, was preserved at a room temperature for one month under nitrogen atmosphere and then its color was measured. Its color was APHA60.

The oxidation conditions and measured results of color of Examples 5 and 8 and Comparative Examples 3 to 4 were shown in Table 2. From the results of Table 2, it was found that a high quality of ε-caprolactone with good color and less change with the lapse of time can be obtained by maintaining the reactivity of 2,4-dimethylbenzaldehyde to 80 mol % or below.

TABLE 1

| Item | Low boiling substance separation column | Rectifying column |
|---|---|---|
| Top section temperature, °C. | 88 | 118 |
| Bottom section temperature, °C. | 125 | 126 |
| Top section pressure, Torr | 15 | 15 |
| Reflux ratio | 2.0 | 2.0 |

TABLE 2

| Item | Example 5 | Comp.Ex.3 | Example 6 | Example 7 | Example 8 | Comp.Ex.4 |
|---|---|---|---|---|---|---|
| Reactivity(mol %) | 61 | 82 | 65 | 72 | 40 | 89 |
| Hold-up time(hr) | 1.0 | 2.4 | 1.0 | 1.0 | 0.5 | 4.0 |
| Temperature(°C.) | 35 | 35 | 45 | 40 | 40 | 40 |
| Catalyst conc.(ppm) | 1.0 | 1.0 | 0.2 | 1.0 | 1.0 | 1.0 |
| Initial color(APHA) | 5 | 10 | 5 | 5 | 5 | 15 |
| Color after one month under nitrogen atmosphere (APHA) | 10 | 30 | 15 | 15 | 10 | 60 |

What is claimed is:

1. A process for producing $\epsilon$-caprolactone which comprises distilling a reaction mixture obtained by oxidation of cyclohexanone to separate impurities, wherein $\epsilon$-caprolactone separated in a rectifying column is contacted with an oxygen-containing gas and then distilled.

2. A process for producing $\epsilon$-caprolactone according to claim 1, which comprises a first distillation step for removing high boiling substances from a reaction mixture obtained by oxidation of cyclohexanone by distillation, a second distillation step for removing low boiling substances and a third distillation step for removing high boiling substances in a rectifying column, and withdrawing high boiling components in a low concentrated state of 5 to 30% by weight in the third distillation step and thus treating it in the first distillation step.

3. A process for producing $\epsilon$-caprolactone according to claim 1, wherein the reaction mixture is obtained by oxidizing a mixture of aromatic aldehyde and cyclohexanone with molecular oxygen in a liquid phase so as to maintain a reactivity of aromatic aldehyde to 80 mol % or below.

4. A process for producing $\epsilon$-caprolactone according to claim 3, wherein the reaction temperature of the liquid phase oxidation is in the range of 20 to 60° C.

5. A process for producing $\epsilon$-caprolactone according to claim 3, wherein the liquid phase oxidation is conducted according to a continuous process and hold-up time is in the range of 10 to 120 minutes.

* * * * *